United States Patent [19]

West et al.

[11] 4,324,901

[45] Apr. 13, 1982

[54] SOLUBLE POLYSILASTYRENE AND METHOD FOR PREPARATION

[75] Inventors: Robert C. West; Lawrence D. David, both of Madison, Wis.

[73] Assignee: Wisconsin Alumni Research Foundation, Madison, Wis.

[21] Appl. No.: 258,663

[22] Filed: Apr. 29, 1981

[51] Int. Cl.³ .............................................. C07F 7/08
[52] U.S. Cl. ................................................... 556/430
[58] Field of Search ....................................... 556/430

[56] References Cited

U.S. PATENT DOCUMENTS 4,052,430 10/1977 Yajima et al. ................... 556/430 X
4,177,230 12/1979 Mazdiyasni .
4,260,780 4/1981 West .................................... 556/430
4,276,424 6/1981 Peterson et al. ................... 556/430

OTHER PUBLICATIONS

C. A. Burkhard, J. Am. Chem. Soc., 71, 963 (1949).
S. Yajima, Y. Hasegawa, J. Hayashi, M. Iimura, J. Mater. Sci., 13, 2569 (1978).

*Primary Examiner*—Paul F. Shaver
*Attorney, Agent, or Firm*—McDougall, Hersh & Scott

[57] ABSTRACT

The preparation of soluble polysilastyrene comprising reacting phenylmethyldichlorosilane and dimethyldichlorosilane in the mole ratio of 1 to 0.25–2 in the solvent solution in the presence of sodium.

11 Claims, 2 Drawing Figures

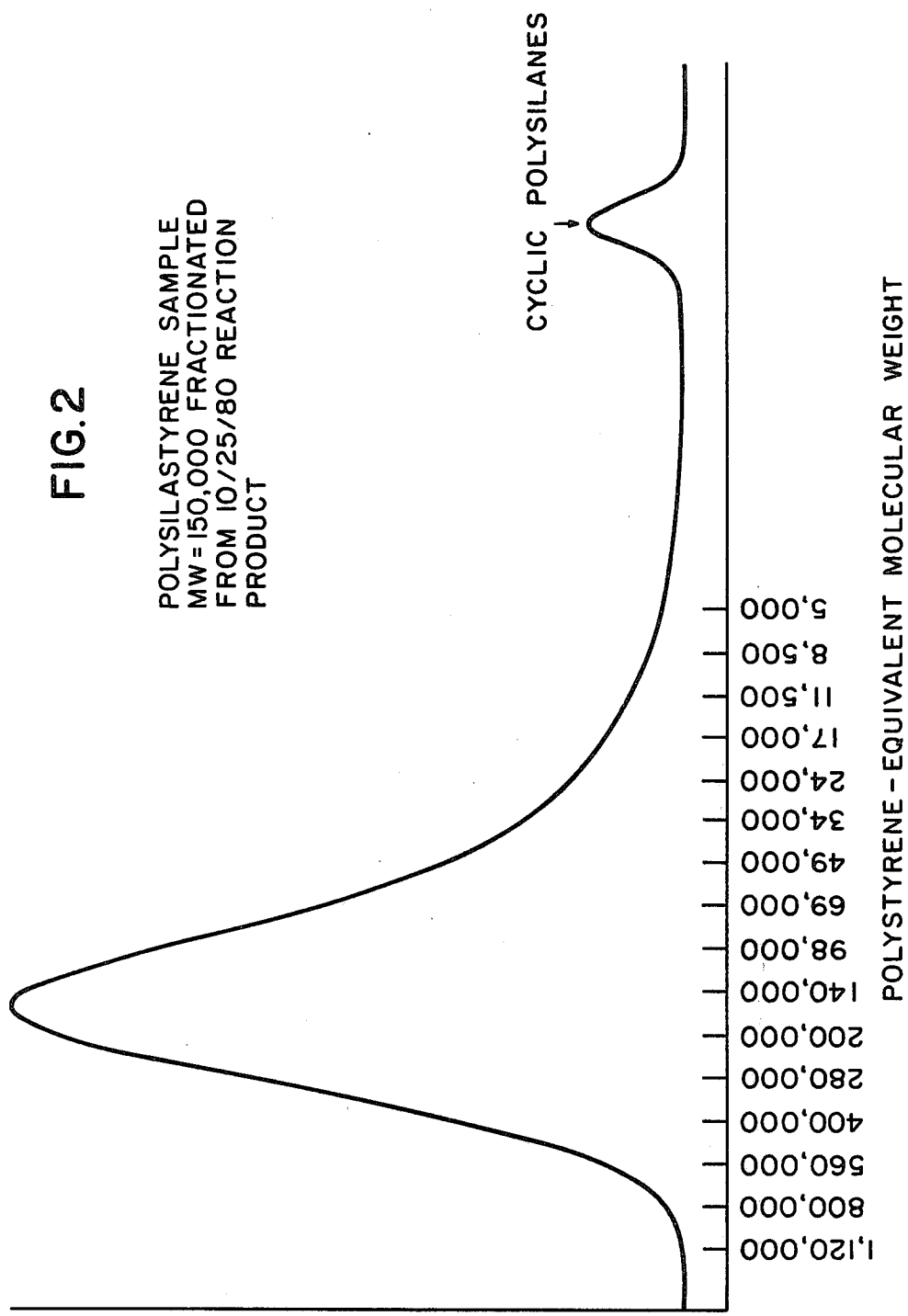

SOLUBLE POLYSILASTYRENE AND METHOD FOR PREPARATION

The Government has rights in this invention pursuant to Contract No. AF0SR 78-3570 awarded by the Department of the Air Force.

FIELD OF THE INVENTION

This invention relates to polysilastyrenes and to a method for the preparation of same.

BACKGROUND OF THE INVENTION

In the copending application of West, Ser. No. 97,778 filed Nov. 27, 1979, now U.S. Pat. No. 4,260,780 and entitled "Phenylmethylpolysilane Polymers and Process for their Preparation", description is made of a process for the preparation of such polymers wherein phenylmethyldichlorosilane and dimethyldichlorosilane are reacted in solvent solution in the presence of a reducing catalyst of sodium, potassium or a sodium potassium alloy, and in the ratio of 1 mole phenylmethyldichlorosilane per 3–20 moles dimethyldichlorosilane. The phenylmethylpolysilane polymers that are produced are characterized by thermoplasticity which enables their formation into fibers and by insolubility which prevents their being taken into solution for use in the formation of films, coatings, and the like.

OBJECTS OF THE INVENTION

It is an object of this invention to provide a method for producing polysilastyrenes of high as well as low molecular weights, which are soluble in ordinary organic solvents to enable the preparation of solutions which can be employed for various film forming, impregnation and coating applications and which enables fractionation for polymer separation based upon molecular weight distribution and which can be produced in relatively high yields.

BRIEF DESCRIPTION OF THE INVENTION

In accordance with the practice of this invention, 1 mole phenylmethyldichlorosilane is reacted with 0.25–2 moles dimethyldichlorosilane in solvent solution in the presence of sodium to produce a polysilastyrene in accordance with the reaction:

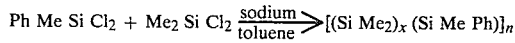

$$Ph\ Me\ Si\ Cl_2 + Me_2\ Si\ Cl_2 \xrightarrow[\text{toluene}]{\text{sodium}} [(Si\ Me_2)_x\ (Si\ Me\ Ph)]_n$$

in which x equals 0.6–1.4 and n is a number up to 1200.

As a solvent, use can be made of any non-acidic solvent, or other solvent that does not react with sodium or with the chlorosilanes, in which the monomers are soluble and which has a boiling point above 100° C. It is preferred to make use of toluene as the solvent since it has a boiling point just above the melting point of the sodium and because it is readily available at low cost; however, other organic solvents, such as xylene, mesitylene, n-octane, decalin, and other higher alkanes can be used.

It is desirable to use sodium alone as the reactant in an amount of 1 to 1.2 moles per mole of Si-Cl. Potassium, when present in small amounts, causes polymer degradation and thus can be employed in such small amounts with sodium when it is desired to produce a lower molecular weight polysilastyrene of waxy consistency. Utilization of potassium in large amounts, as in the form of a sodium-potassium alloy (78% K) or pure potassium, as in the aforementioned application, will result in extensive cross linking to produce an insoluble and infusible polymer. Thus the amount of potassium should not exceed 1% by weight.

In the preferred practice of the invention, the monomers are mixed for reaction in substantially equal molecular proportions and the reaction to produce the polymer is carried out at reflux temperature, and preferably at a temperature of about 100° C. for a period of time that may range up to 24 hours. Higher temperatures up to 150° C. can be employed but without any distinct advantage from the standpoint of reaction rate.

DESCRIPTION OF THE DRAWINGS

FIG. 2 is an example of a molecular weight distribution curve of the polysilastyrene polymers produced by this invention.

DETAILED DESCRIPTION OF THE INVENTION

Figure 1:
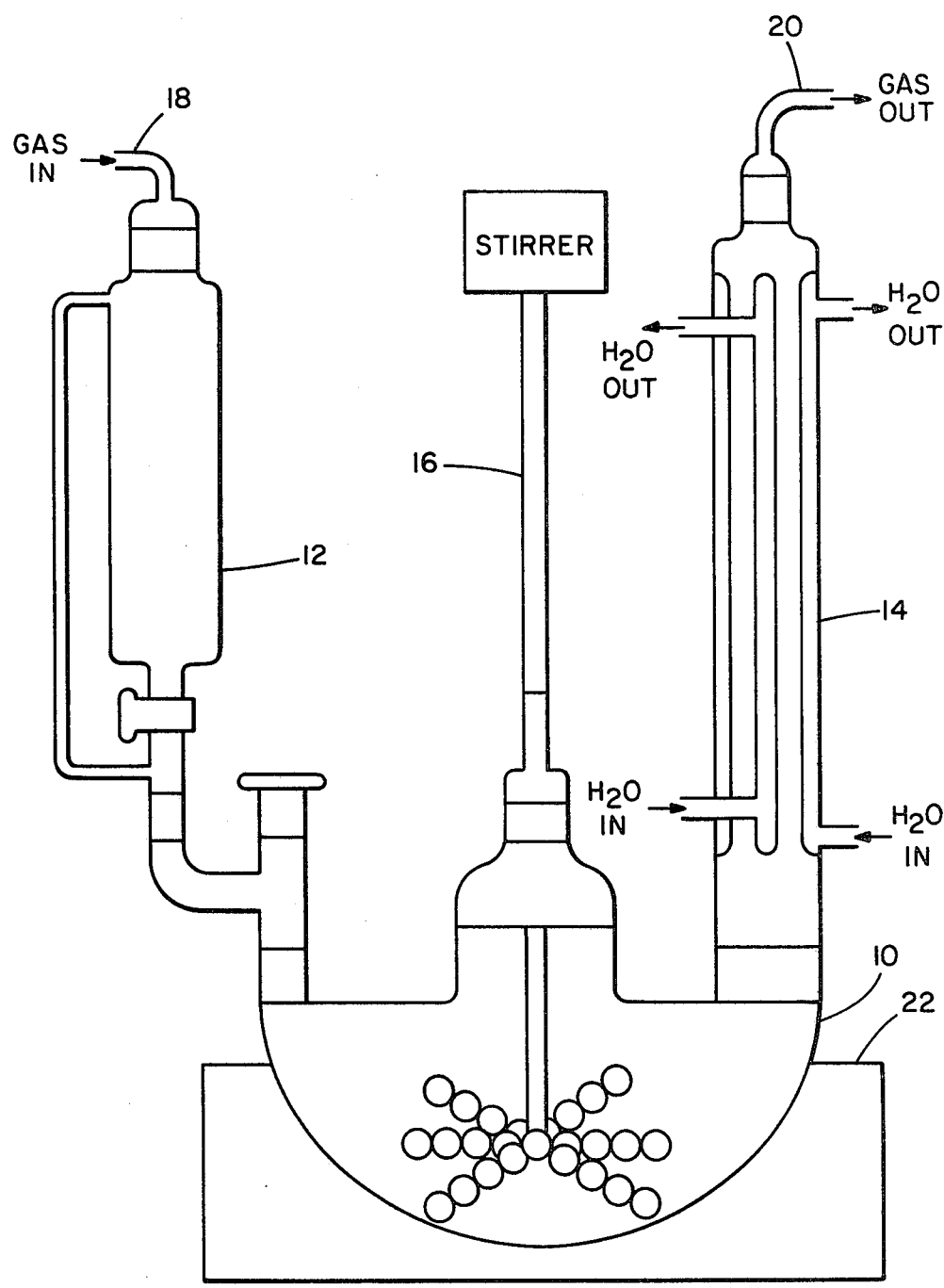
FIG. 1 of the drawings is an illustration of a laboratory setup for the preparation of polysilastyrene polymers in accordance with the practice of this invention.

Having described the broad concepts of the invention, a detailed description will hereinafter be made by way of the following example.

An assembly is made of a 2 liter, 3-necked flask 10 a 500 ml. addition funnel 12, a Davies double jacketed condenser 14, and a motor driven stirrer 16, as illustrated in the FIG. 1 of the drawing. The reaction is carried out in an inert atmosphere of dry nitrogen or argon which is circulated through the flask from a gas inlet 18 to a gas outlet 20.

600 ml of dry toluene, which has been dried by refluxing over sodium, is introduced through the funnel 12 into the flask. 48.3 grams of sodium, in the form of chunks or peas (available from Aldrich Chemical in a size of 5 mm diameter or less), corresponding to a 5% molar excess is added to the toluene and heated to boiling temperature with stirring to disperse the sodium in the solvent. 60.5 ml dimethyldichlorosilane ($\frac{1}{2}$ mole) and 80.5 ml phenylmethyldichlorosilane ($\frac{1}{2}$ mole) are introduced with stirring and the flask is heated to nearly 100° C. in a heating mantle 22 to initiate the reaction.

Reflux temperature is maintained by lowering the heating mantle from the flask when the chlorosilanes are added rapidly enough for exothermic reaction. Addition of the chlorosilane should be completed within a 15 minute period.

The beginning of the reaction is indicated by the presence of a dark blue color. Since the polysilastyrene is photosensitive in solution, it is desirable to shield the flask from light, as by covering the flask with aluminum foil.

Refluxing is continued with gentle stirring for about 10 hours after which the reaction is quenched by cooling the flask to room temperature and by slow addition of ethanol (95%). Addition is then made of an aqueous solution of sodium bicarbonate and/or an aqueous solution of ammonium chloride to discharge the blue color. The mixture is agitated until the color of the formed organic layer turns milky white. In the event that the blue color remains, the organic layer can be separated from the aqueous layer and fresh aqueous sodium bicarbonate added thereto with stirring.

For purification, the separated organic layer is stripped of solvent, as by vacuum distillation, and the polymer remaining is washed with water to remove salt residues. At all times the organic layer is protected from light.

The resulting polymer, obtained in a yield of about 90% or more, can be fractionated, as by solvent separation in xylene, to leave a polysilastyrene residue that is soluble in hydrocarbon solvents and especially tetrahydrofuran. The polysilastyrene can be fractionated from a tetrahydrofuran-isopropanol system to give high molecular weight fraction numbers averaging as much as 350,000 molecular weight, and oligomers in the form of a viscous oil.

The yield is typically 60% polymer and about 30% cyclic oligomers having the formula $$Si_5Me_{10-x}Ph_x \text{ in which } x=0-4$$

At least 90% by weight of the formed polymer is soluble in an organic solvent such as alkylbenzenes, chlorocarbons and tetrahydrofuranes. A molecular weight distribution curve obtained from a gel permeation chromatograph of the polysilastyrene polymer using an ultraviolet detector set at 254 nm and prepared by the process described is shown in FIG. 2 of the drawings.

The polysilastyrene polymers prepared in accordance with the practice of this invention can be formed into solids, films, fibers or the polymer can be molded, cast, or spun from hot melt or from solution in suitable solvents.

The polysilastyrene polymers of this invention can be used as percursors for making silicon carbide fibers, as described in the aforementioned copending application. The polymers can be formed into fibers, sheets and bulk shapes followed by thermolysis under inert conditions at temperatures of about 1200° C. to convert the polymer to silicon carbide in fiber, sheet and bulk shape form as represented by the following equation:

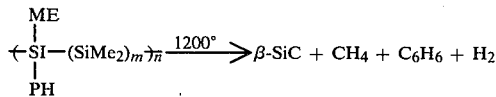

The polymers of this invention also find beneficial use in gas chromatography separation phases. Inert supports coated with the polysilastyrene can be used as a packaging in columns for separation of gas streams composed of mixtures of nonpolar compounds at temperatures for the polysilastyrene such as 300° C.

Polysilastyrene powders of less than 40 μ are suitable for use in liquid chromatography wherein use is made of a carrier in the form of a solvent in which the polymer is inert, such as alcohol, pentane, methyl cyanide or water.

As previously described, the polysilastyrene polymers of this invention can be dissolved in suitable solvents, such as carbon tetrachloride, toluene, or tetrahydrofuran for use as a coating material or as an impregnating material. It is particularly suitable for use as a coating for siliceous materials wherein a strong bonding relation can be established with the silicon oxide groups at the surface of the siliceous material. Ceramics can be strengthened by coating or impregnating with the polymers of this invention and subsequent firing to transform the polymer into silicon carbide.

Thin films which can be formed of the polysilastyrene polymers of this invention, as by pressure molding or casting from solution are characterized as good insulators ($\sigma < 10^{-12} \Omega^{-1} cm^{-1}$ conductivity) while the conductivity can be increased materially by doping with antimonypentafluoride ($SbF_5$) or arsenic pentafluoride ($AsF_5$).

It will be understood that changes may be made in the details of formulation and operation, without departing from the spirit of the invention, especially as defined in the following claims.

We claim:

1. Process for making polysilastyrenes comprising reacting phenylmethyldichlorosilane and dimethyldichlorosilane in solvent solution in the presence of sodium in the ratio of 1 mole phenylmethyldichlorosilane to 0.25-2 moles dimethyldichlorosilane.

2. The process as claimed in claim 1 in which the monomers are reacted in about equal molecular proportions.

3. The process as claimed in claim 1 in which the reaction is carried out at a temperature above the melting point temperature of the sodium.

4. The process as claimed in claim 1 in which the reaction is carried out at a temperature within the range of 100°–150° C.

5. The process as claimed in claim 1 in which the solvent is a non-acidic solvent having a boiling point of at least 100° C. and is inert to the sodium and to the chlorosilanes.

6. The process as claimed in claim 1 in which the reaction is carried out at reflux temperature.

7. The process as claimed in claim 1 in which the sodium is employed at a slight excess of up to 20 mole percent.

8. The process as claimed in claim 1 which includes potassium in an amount up to 1% by weight of the sodium.

9. The process as claimed in claim 1 which includes the step of protecting the reaction from light.

10. The process as claimed in claim 1 in which the reaction is carried out in an inert atmosphere.

11. A polysilastyrene produced by the process of claim 1 having the general formula $$[(Si-Me_2)_x (Si-Me-Ph)]_n$$

in which x equals 0.6–1.4 and n is a number up to 1200.

* * * * *